United States Patent

Barlow

Patent Number: 5,338,299
Date of Patent: Aug. 16, 1994

[54] BALLOON CATHETER

[75] Inventor: Edward A. Barlow, Bloomington, Minn.

[73] Assignee: Angeion Corporation, Plymouth, Minn.

[21] Appl. No.: 953,481

[22] Filed: Sep. 29, 1992

Related U.S. Application Data

[63] Continuation-in-part of Ser. No. 871,722, Apr. 21, 1992, Pat. No. 5,171,297, which is a continuation of Ser. No. 324,913, Mar. 17, 1989, Pat. No. 5,112,304.

[51] Int. Cl.$^5$ ............................................. A61M 29/00
[52] U.S. Cl. ...................................... 604/96; 604/103; 606/192; 606/194
[58] Field of Search ............................ 604/96, 97, 98, 99, 604/100, 101, 102, 103, 280, 283; 606/191, 192, 194, 195; 128/657

[56] References Cited

U.S. PATENT DOCUMENTS

| 4,456,000 | 6/1984 | Schjeldahl et al. | 604/53 |
| 4,637,396 | 1/1987 | Cook . | |
| 4,702,252 | 10/1987 | Brooks et al. . | |
| 4,762,130 | 8/1988 | Fogarty et al. | 604/96 |
| 5,167,239 | 12/1992 | Cohen et al. | 128/657 |
| 5,176,637 | 1/1993 | Sagae | 604/96 |

*Primary Examiner*—C. Fred Rosenbaum
*Assistant Examiner*—Noelle Kent Gring
*Attorney, Agent, or Firm*—Hugh D. Jaeger

[57] ABSTRACT

A balloon consisting of braided fibers encapsulated between two plastic elastomeric materials affixes to a distal end of a catheter. The braided fibers provide reinforcement to contain pressure and determine the maximum diameter of the balloon on expansion. The elastomeric material provides for fluid containment and collapsing of the balloon after pressurization. An embedded spring in an elastomeric material internal to the catheter provides memory to assist in collapsing the balloon after pressurization. The embedded spring extends from the distal end of the catheter towards the proximal end of the catheter along a substantial length of the catheter. The catheter with the balloon are in a multilumen configuration or in a coaxial configuration. A guidewire passage extends through the elastomeric material with the embedded spring. An alternative embodiment illustrates a hub with a movable internal seal and inner tube connected to a balloon catheter tip with a free space collapsement spring. The movable inner seal also assists in spring collapsement and in shortening of the balloon structure for maximum allowable radial inflation. A distal portion of a balloon catheter includes a compressible spring which is free floating within a tubular interior area and having no embedding material about it.

19 Claims, 13 Drawing Sheets

BALLOON CATHETER

CROSS REFERENCES TO CO-PENDING APPLICATIONS

This patent application is a continuation-in-part of U.S. Ser. No. 07/871,722, filed Apr. 21, 1992, now U.S. Pat. No. 5,171,297 entitled "Balloon Catheter", which is a continuation of U.S. Ser. No. 07/324,913, filed Mar. 17, 1989, now U.S. Pat. No. 5,112,304 allowed, both assigned to the same assignee as the present patent application.

BACKGROUND OF THE INVENTION

1. Field of the Invention

The present invention pertains to a surgical catheter, and more particularly, a balloon catheter for enlargement of restrictions in blood vessels, arteries or other human tissue.

2. Description of the Prior Art

Prior art balloon catheters have utilized numerous types of structures to expand outwardly to enlarge a restriction such as in a blood vessel, an artery or human tissue, such as the prostrate. One problem in the past with these structures which enlarged on inflation was that the structure did not always return to its original diameter or initial circular configuration.

U.S. Pat. No. 4,456,000 to Sehjeldahl uses a thin rigid material affixed to the distal end of a catheter to form the balloon. Particularly in the use of non-distensible balloons, the initial profiles achieved by wrapping the balloon are much larger than the outer diameter of the catheter shaft and after inflation in the body, the resulting collapsed profile may appear in cross section as a plate extending outward from the center of the catheter. This necessitates use of a larger device to introduce the balloon catheter and presents complication on removal of the device from the body and may potentially damage tissue.

U.S. Pat. No. 4,637,396 to Cook uses a knitted balloon in which the knitting changes shape to accommodate balloon expansion. This allows for higher pressures to be achieved in larger diameter balloons, but does not necessarily deal with initial or collapsed profiles.

U.S. Pat. No. 4,702,252 to Brooks uses a braided balloon which changes in length as it expands and is accomplished by a spring at the proximal hub end of the catheter. This design requires relative motion between various members of the catheter which may be difficult in long length and tortuous passageways.

U.S. Pat. No. 4,762,130 to Fogarty uses an embedded spring to lower the profiles of the balloon. This design also requires relative motion along its length and does not enhance the pressure changing capability of the elastomeric materials.

Hubs incorporated in balloon catheters have on occasion exhibited balloon pressure integrity breakdown where pressure is bled off through various sealment members of the hub. One alternative embodiment discloses an additional sealing member within an inner chamber of the hub to provide ample pressure maintaining capabilities for proper and constant pressure balloon inflation.

The present invention overcomes the disadvantages of the prior art by providing a balloon catheter with braided fibers encapsulated between elastomeric materials and an embedded spring to provide a low balloon profile after pressurization and depressurization.

The present invention also overcomes other disadvantages of the prior art by providing a collapsible spring fixed between the movable points for allowing a greater inflational radius.

SUMMARY OF THE INVENTION

The general purpose of the present invention is to provide a balloon catheter which has a low profile in a deflated state after pressurization to a maximum diameter, and has no components which move relative to one another.

According to one embodiment of the present invention, there is provided a balloon catheter with a hub at a proximal end including a guidewire entry port, an inflation/deflation port and a tube connected to the hub. A guidewire passage and an inflation/deflation passage extend along the length of the tube. An embedded spring in an elastomeric material or like material connects to the distal end of the tube. A balloon, including braided fibers encapsulated between an outer elastomeric material and inner elastomeric material, connects between the end of the tube and the distal end of the embedded spring member. The catheter can assume either a multilumen configuration or a coaxial configuration.

According to an alternative embodiment of the present invention, there is provided a hub for use with a balloon catheter having an additional seal incorporating an 0-ring aligned about a piston in direct contact with an internal chamber of the hub, thus providing a seal to contain pressurized fluid.

According to another alternative embodiment of the present invention, there is provided a balloon catheter distal end incorporating a free space spring having unrestricted movement for the purpose of returning a balloon to its streamlined relaxed position after it has been inflated. The tip member is connected by a movable tube connected to a piston member, which assists in negation of the spring function during inflation, as well as shortening of the distal tip area length to allow for greater radiused inflation.

Significant aspects and features of the present invention include a low profile balloon before and after pressurization to its maximum diameter. The differential between the balloon structure and the inner member of the catheter is minimal, even after pressurization and subsequent depressurization because of the combined action of the internal spring and the elastomeric material of the balloon. The pliability of the elastomeric material and the spring also provide enhanced steering of the catheter during placement due to its extreme flexibility and soft tip.

Other significant aspects and features of the present invention is the ability to achieve higher balloon pressures, especially in larger sized balloons used in larger vessels, arteries or tissues.

Further significant aspects and features of the present invention include a braided fiber member which expands to a fixed diameter on inflation with enhanced pressure conveying capability. The braided fibers assist the balloon to collapse to approximately the same profile after pressurization. Additionally, there is enhanced cyclic durability because of the elastomeric materials.

In addition, the use of fibers and elastomeric materials in the balloon construction provides for a softer distal tip to the catheter, enhancing steerability and reducing trauma. In addition, the elastomeric material provides a construction which enhances its ability to withstand repeated cycles of pressurization and depressurization.

In addition, the braid can be made of a radiopaque material obviating the need for specific bands for locating the balloon in the body under fluoroscopy.

Lastly, the embedded spring also provides structural integrity against collapse of the inner member of the catheter during pressurization of the balloon. This enhanced ability allows for movement of the guidewire while the balloon is pressurized.

Yet a further significant aspect and feature of the present invention includes a connecting tube between the sealing member piston to distend the balloon catheter in a proximal direction where the effect of spring tension along the balloon structure is relaxed and negated.

Still another significant aspect and feature of the present invention is a balloon structure whose length is essentially shortened, thus allowing a greater radius of inflation.

Having thus described embodiments of the present invention, it is a principal object hereof to provide a balloon catheter with a balloon using braided fibers or like materials disposed between an inner and an outer elastomeric layer.

One object of the present invention is to provide a multilumen balloon configuration or a coaxial balloon configuration.

Another object of the present invention is to provide a balloon catheter which includes internal structure which functions to deflate and collapse the balloon after pressurization to its maximum diameter. The balloon with braided fibers between the elastomeric material returns to its normal position, and a spring embedded in an elastomeric material of the distal end of the catheter further functions to collapse and return the balloon to a normal, deflated position after pressurization. A material with a like function can also be utilized in place of the spring.

Another object of the present invention is to provide a spring structure bonded at its ends and at movable points and in a tubular area which functions to deflate and collapse the balloon after pressurization to its maximum diameter. The balloon structure with braided fibers between the elastomeric material returns to its normal position aided by the spring which is unrestricted in movement.

Another object of the present invention is to provide a hub having sized piston length to help determine the maximum radius of balloon structure inflation.

Another object of the present invention is to provide a well sealed leak proof hub for maintaining proper inflational pressures.

BRIEF DESCRIPTION OF THE DRAWINGS

Other objects of the present invention and many of the attendant advantages of the present invention will be readily appreciated as the same becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
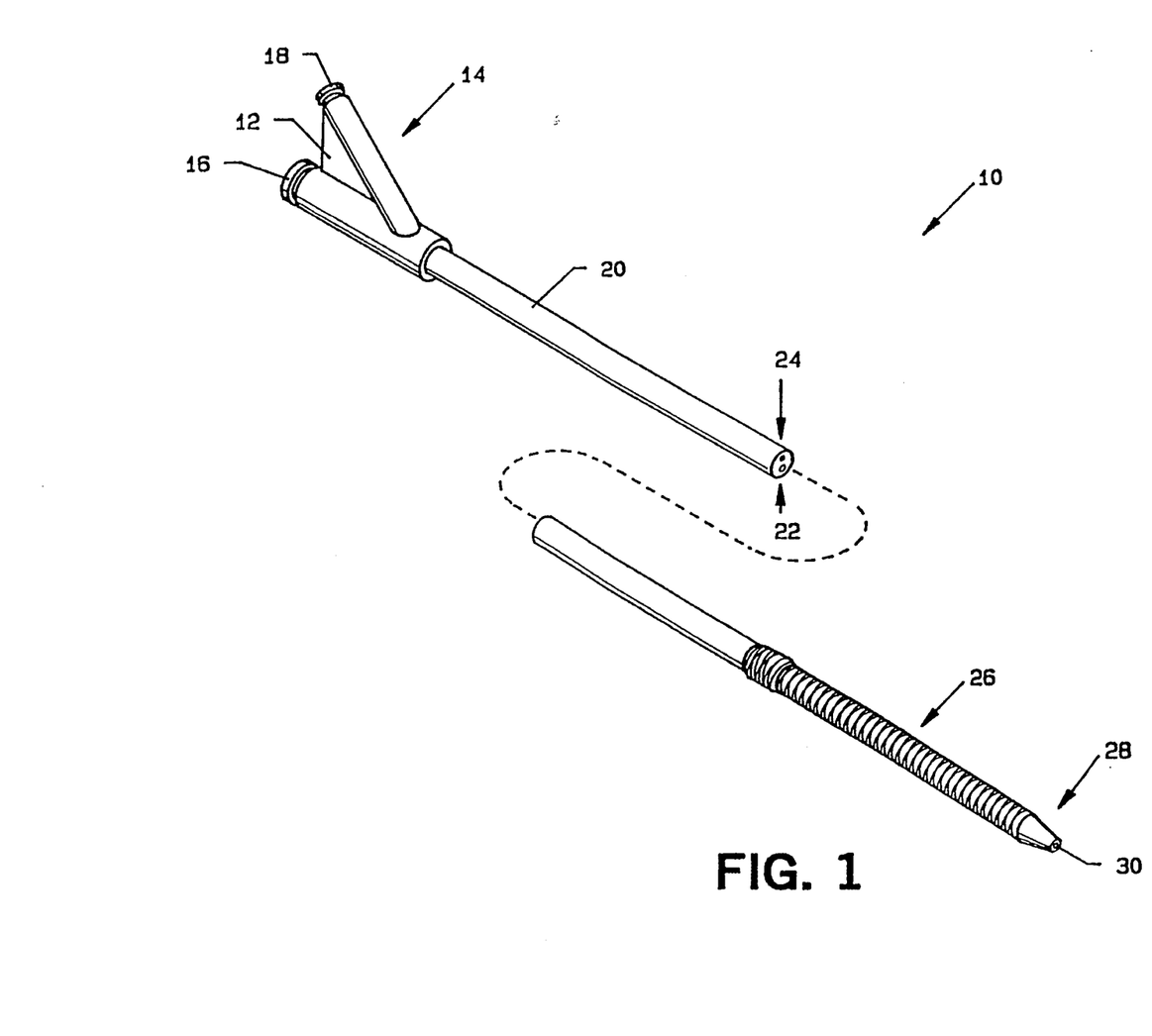
FIG. 1 illustrates a perspective view of a multilumen balloon catheter, the present invention.

FIG. 1 illustrates a perspective view of a multilumen balloon catheter 10, the present invention, including a hub 12 at a proximal end 14 with guidewire entry port 16 and an inflation/deflation port 18. This particular multilumen configuration is bilumen. A catheter tube 20 connects to the hub 12, and includes a guidewire passage 22 and an inflation/deflation passage 24. A balloon structure 26, as later described in detail, secures about the distal end 28. A guidewire exit 30 is at the distal end 28 of the balloon structure 26.

Figure 2:
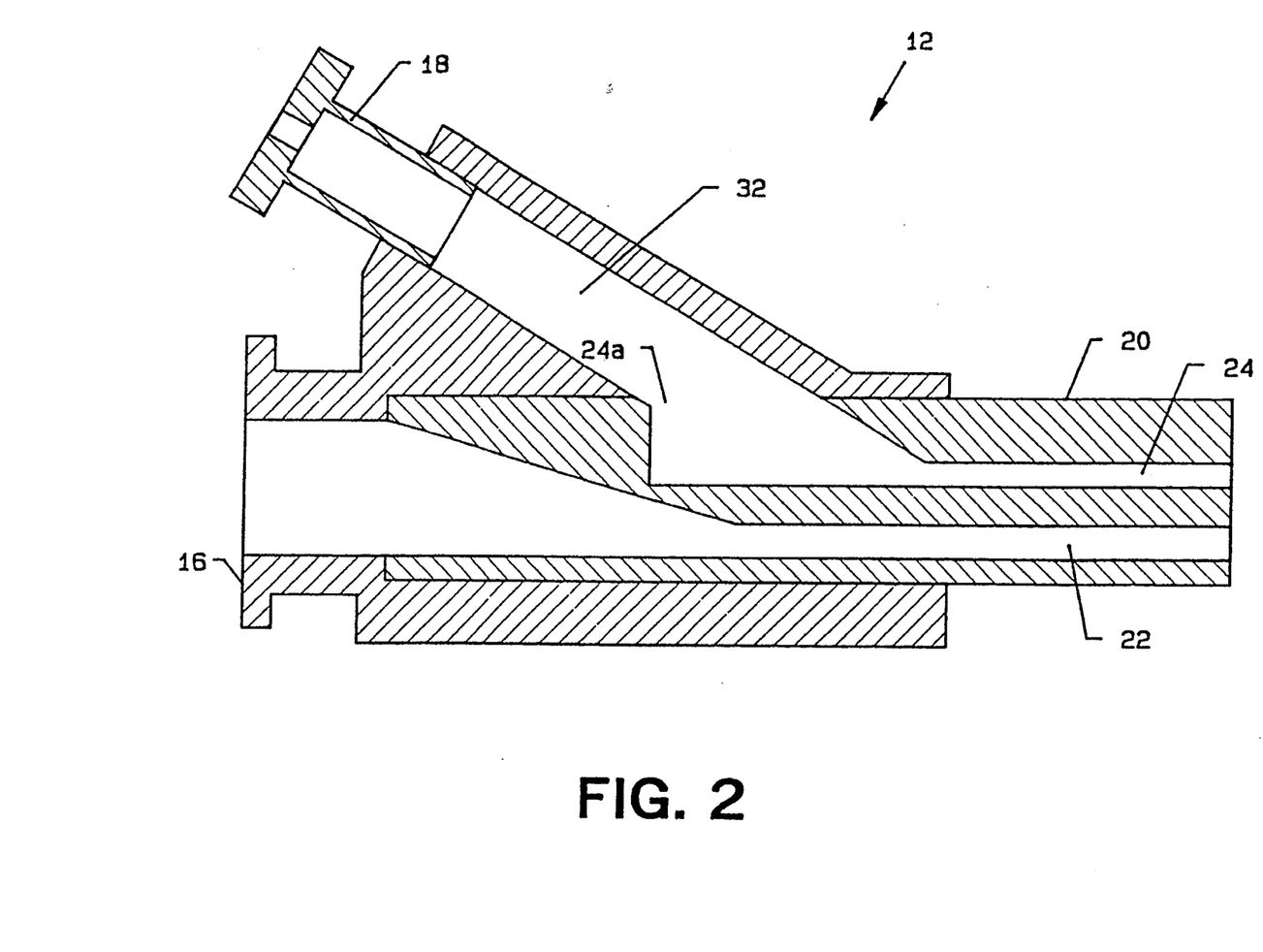
FIG. 2 illustrates a cross-sectional view of the hub of the multilumen configuration.

FIG. 2 illustrates a cross-sectional view of the hub 12 where all numerals correspond to those elements previously described. The figure illustrates the hub 12 being a molded thermoplastic member engaged about the catheter tube 20, and fused or adhesively secured thereto. The hub 12 includes a hub chamber 32, an inflation/deflation port 18, and a guidewire entry port 16. The proximal end of the catheter tube 20 secures into one end of the guidewire entry port 16. The hub 12, the catheter tube 20, the guidewire entry port 16 and the inflation/deflation port 18 are assembled by known processes. The guidewire passage 22, internal to the catheter tube 20, connects between the guidewire entry port 16 and the balloon structure 26 of FIG. 3. The inflation/deflation passage 24 connects the balloon structure 26 to the inflation/deflation port 18 through an angled passageway 24a and the hub chamber 32.

Figure 3:
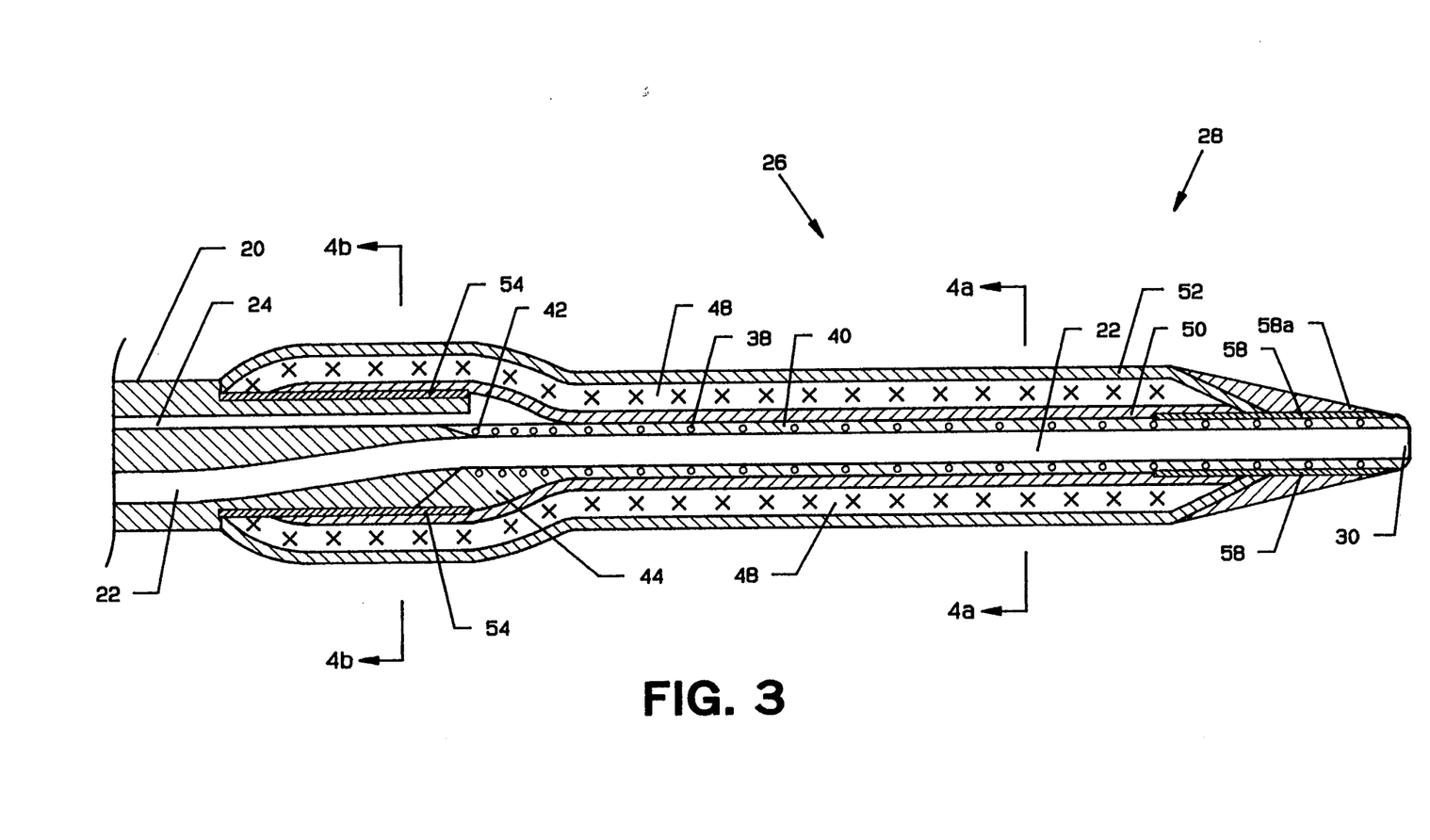
FIG. 3 illustrates a cross-sectional view of the distal end of the multilumen configuration.

FIG. 3 illustrates a cross-sectional view of the distal end 28 of the balloon catheter 10. An embedded spring 38 is embedded or fused into elastomeric material 40 which connects to the catheter tube 20 at point 44, such as by heat fusion or adhesively. The spring can be tensioned to a predetermined degree prior to being embedded in the elastomeric material providing a memory for the embedded spring 38 in the elastomeric material. A balloon structure 26, which is coaxial, includes a braided fiber 48 between an inner elastomeric material 50 and outer elastomeric material 52, which is secured about point 54 of the catheter tube 20 and about point 58 of the embedded spring 38 and elastomeric material 40 containing the guidewire passage 22, such as by heat fusion or adhesively. The molded tip 58a provides flexibility and softness of the catheter.

Figure 4A:
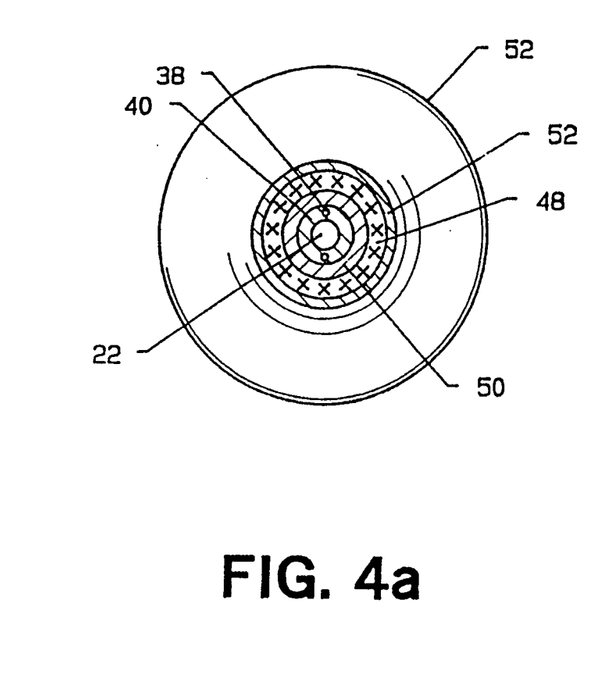
FIG. 4A illustrates a cross-sectional view taken along line 4a–4a of FIG. 3 of the multilumen configuration.

FIG. 4A illustrates a cross-sectional view taken along line 4a–4a of FIG. 3 where all numerals correspond to those elements previously described.

Figure 4B:
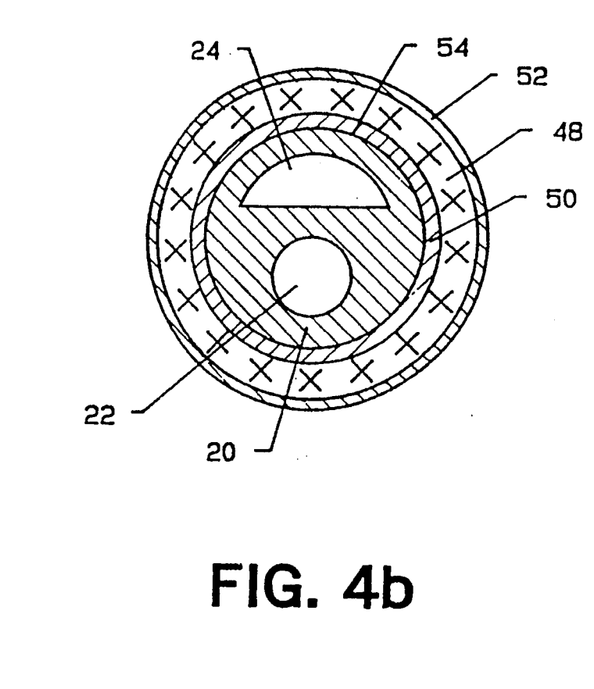
FIG. 4B illustrates a cross-sectional view taken along line 4b–4b of FIG. 3 of the multilumen configuration.

FIG. 4B illustrates a cross-sectional view taken along line 4b–4b of FIG. 3 where all numerals correspond to those elements previously described.

Figure 5:
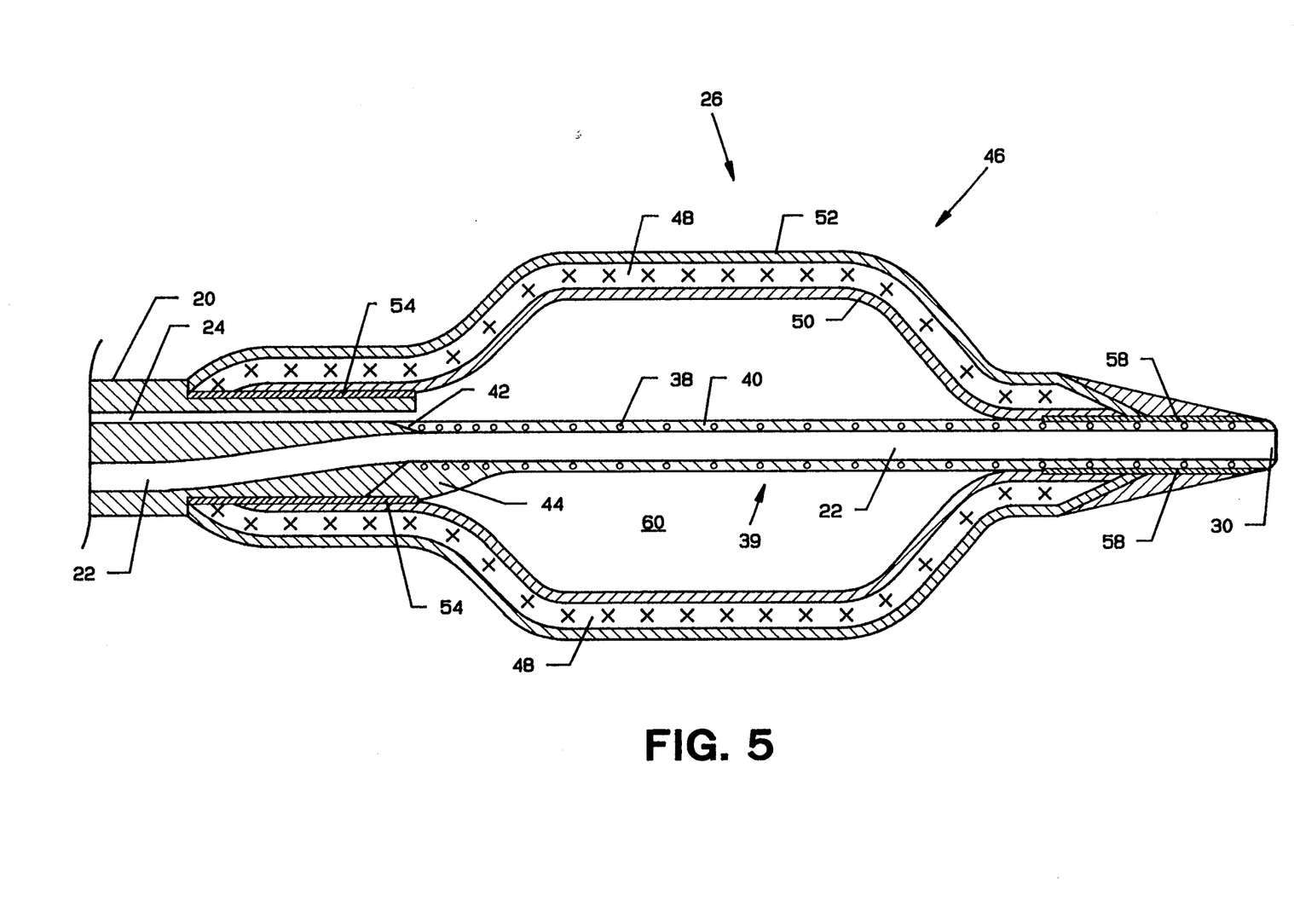
FIG. 5 illustrates the expanded balloon of the multilumen configuration.

FIG. 5 illustrates the balloon catheter 10, and particularly, the balloon structure 26 in an inflated balloon position 46. All numerals correspond to those elements previously described. The embedded spring 38 is compressed longitudinally and the braided fiber 48 has been expanded outwardly so as to enlarge along a substantial portion of its length centered at approximately the midpoint of the longitudinal length of the braided fibers. The outward expansion of the braided fibers 48 effectively shortens the length of the balloon 26 in a direction towards the proximal end 14 causing the embedded spring 38 to compress in a like direction. The braided fibers 48 provide for expansion to a predetermined diameter for the balloon, and form a cavity 60 about the inner surfaces of the balloon structure 26 and the member with the embedded spring 38. After deflation of the inflated balloon position 46 and placing a vacuum on the inflated balloon position 46 through the inflation/deflation port 18, the elastomeric materials 50 and 52 about the braided fibers 48 in combination, provide for collapsing of the balloon, as well as the embedded spring 38 returning to a normal resting position. Likewise, the memory of the elastomeric material materials 50 and 52 and the embedded spring 38 secondarily assist the balloon structure in returning to a predetermined collapsed condition. Materials of known elasticity can be selected such that the braided fibers or the spring may not be required. The elastomeric materials can also be selected to have different degrees of elasticity for expansion and subsequent contraction.

MODE OF OPERATION

Referring to FIGS. 1–5, during a typical procedure, a guidewire is placed through a body tube or tissue to be dilated, typically an artery. The balloon catheter 10 is then introduced over the guidewire by placing the distal end 28 of the catheter over the proximal end of a guidewire. The balloon catheter 10 is then moved into a position of restriction by moving the catheter over the guidewire. Once in position, a syringe filled with a radiopaque fluid is attached to the inflation/deflation port 18 and the syringe plunger moved inward to inflate and pressurize the inflated balloon position 46 by passing radiopaque fluid through the inflation/deflation passage 24 and into the cavity 60 to expand the balloon structure 26 outwardly to a desired intermediate expansion point or to a maximum expansion point allowed by the weave structure of the braided fibers 48. After inflation, a vacuum is introduced into the balloon by moving the plunger outward. The balloon then returns to its resting position. The catheter is then removed from the body. The balloon is caused to return to its normal deflated position by the braided fibers seeking to return to a resting position, the elasticity of the materials and the embedded spring 38.

DESCRIPTION OF THE ALTERNATIVE EMBODIMENTS

Figure 6:
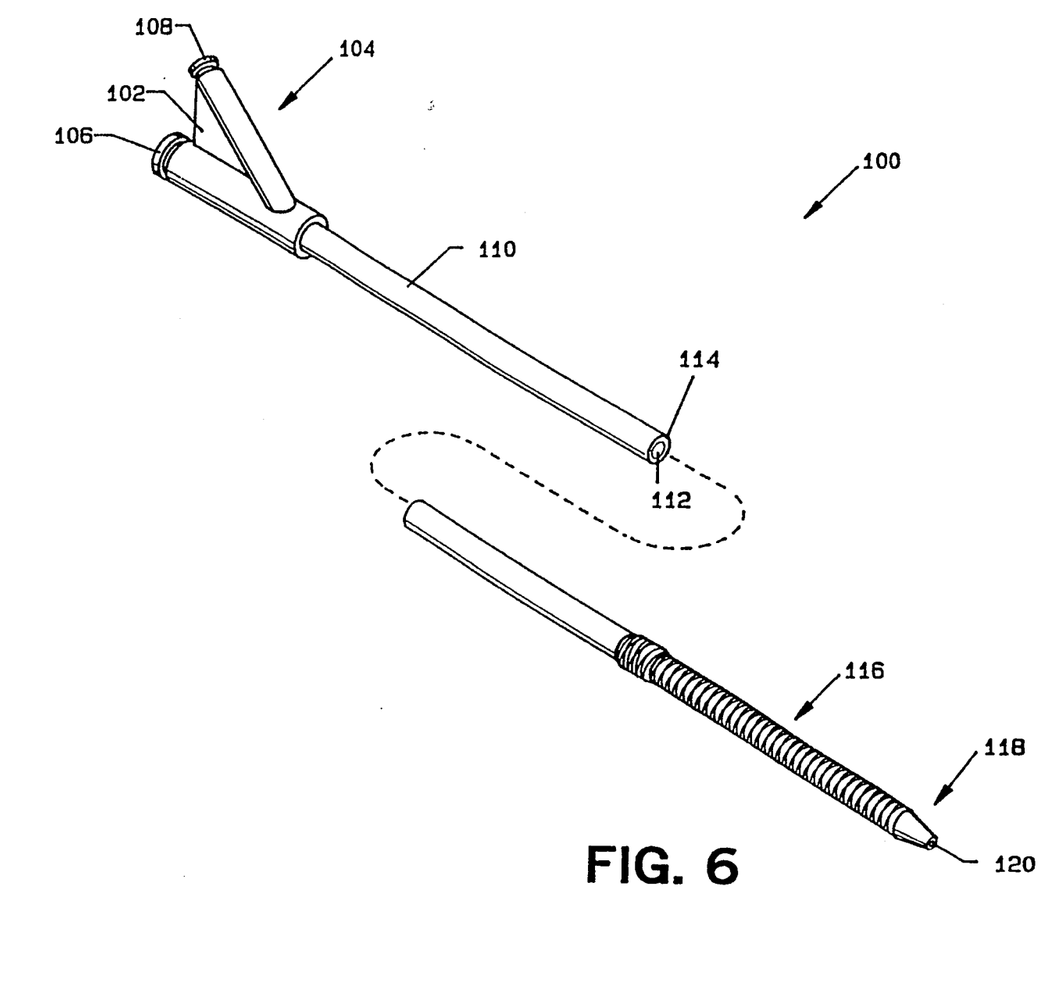
FIG. 6 illustrates a perspective view of a coaxial balloon catheter, an alternative embodiment of the present invention of the coaxial configuration.

FIG. 6 illustrates a perspective view of a coaxial balloon catheter 100, an alternative embodiment of the present invention, including a hub 102 at a proximal end 104 with guidewire entry port 106 and an inflation/deflation port 108. A coaxial catheter tube 110 connects to the hub 102, and includes a guidewire passage 112 and an inflation/deflation passage 114. A balloon structure 116, as later described in detail, secures about the distal end 118. A guidewire exit 120 is at the distal end 118 of the tube 110. The principles of the alternative embodiment are like those as described in FIGS. 1–5.

Figure 7:
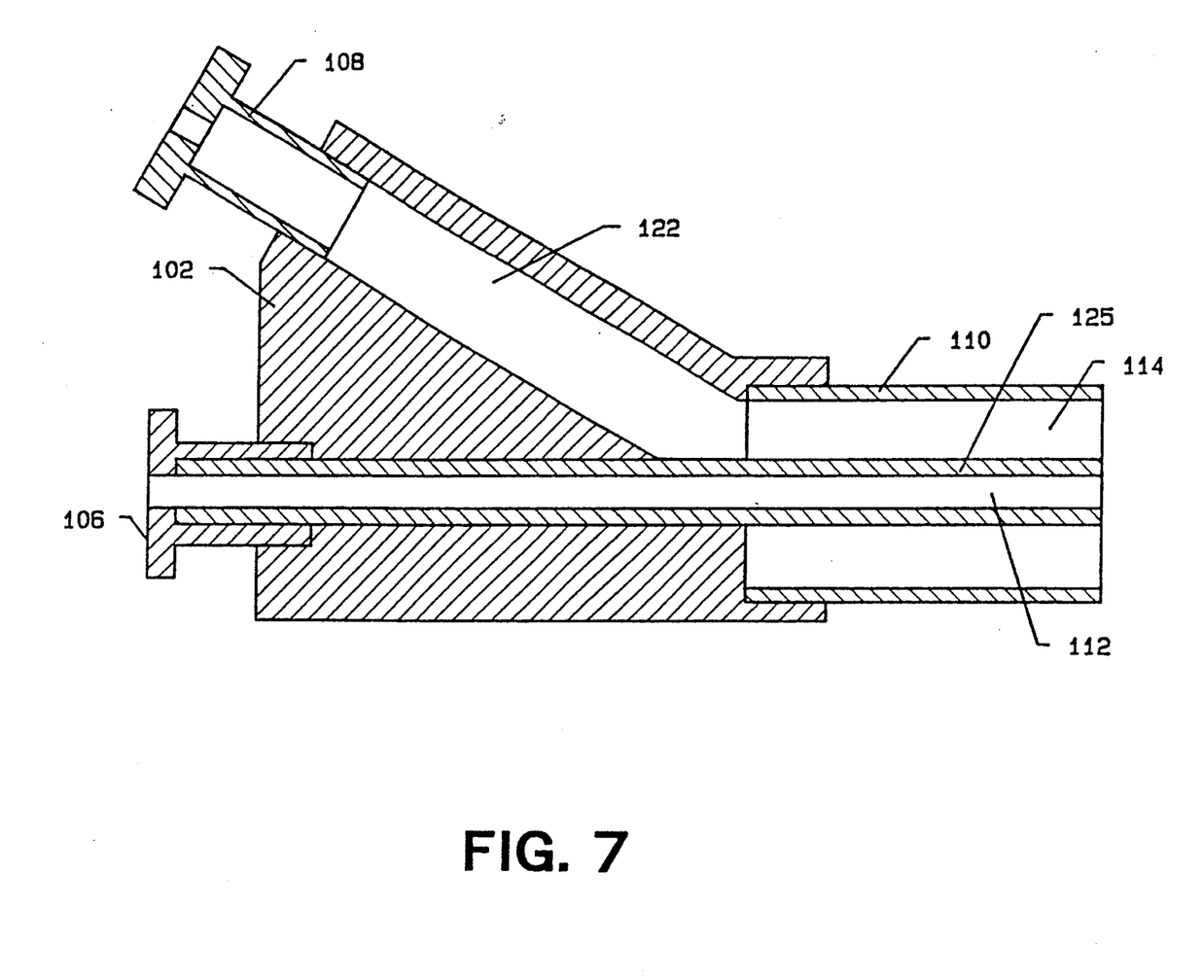
FIG. 7 illustrates a cross-sectional view of the hub of the coaxial configuration.

FIG. 7 illustrates a cross-sectional view of the hub 102 where all numerals correspond to those elements previously described. The figure illustrates the hub 102 being a molded member engaged about the tube 110 and fused or adhesively secured thereto. The hub 102 includes a hub chamber 122, an inflation/deflation port 108, and a guidewire entry port 106 secured into the hub 102. The proximal end of the tube 110 secures into one end of the guidewire entry port 106. The hub 102, the tube 110, the guidewire entry port 106 and the inflation/deflation entry port 108 are assembled by known processes. An inner coaxially aligned tube 125 forms the guidewire passage 112 and connects between the guidewire entry port 106 and the balloon structure 116 of FIG. 8. The inflation/deflation passage 114 is formed between the walls of the tube 110 and the elastomeric material 125 in a coaxial fashion. The inflation/deflation passage 114 connects the balloon structure 116 to the inflation/deflation port 108 through the hub chamber 122 as illustrated in FIG. 8.

Figure 8:
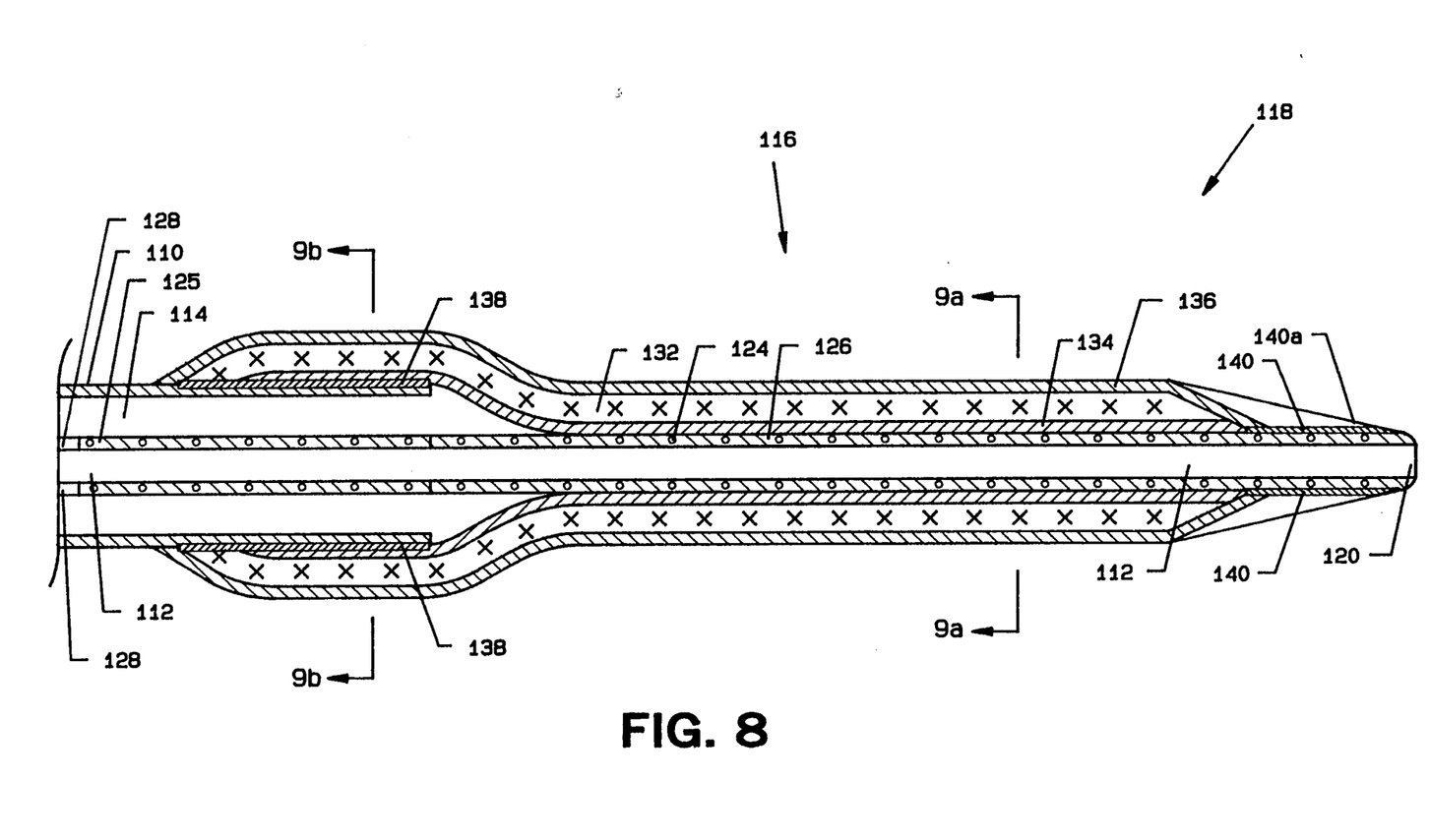
FIG. 8 illustrates a cross-sectional view of the distal end of the coaxial configuration.

FIG. 8 illustrates a cross-sectional view of the distal end 118 of the balloon catheter 100. An embedded spring 124 is embedded in elastomeric material 126 which connects to the tube 110 at point 128, such as by heat fusion or adhesive. The embedded spring 124 can be tensioned to a predetermined degree prior to being embedded in the elastomeric material providing a memory for the embedded spring in the elastomeric material. A balloon structure 116 which is coaxial includes an inner braided fiber 132 between an inner elastomeric material 134 and an outer elastomeric material 136, secures about point 138 of the tube 110 and about point 140 of the embedded spring 124 and inner elastomeric material 126 containing the guidewire passage 112 such as by heat fusion or adhesively. The molded tip 140a provides flexibility and softness of the catheter.

Figure 9A:
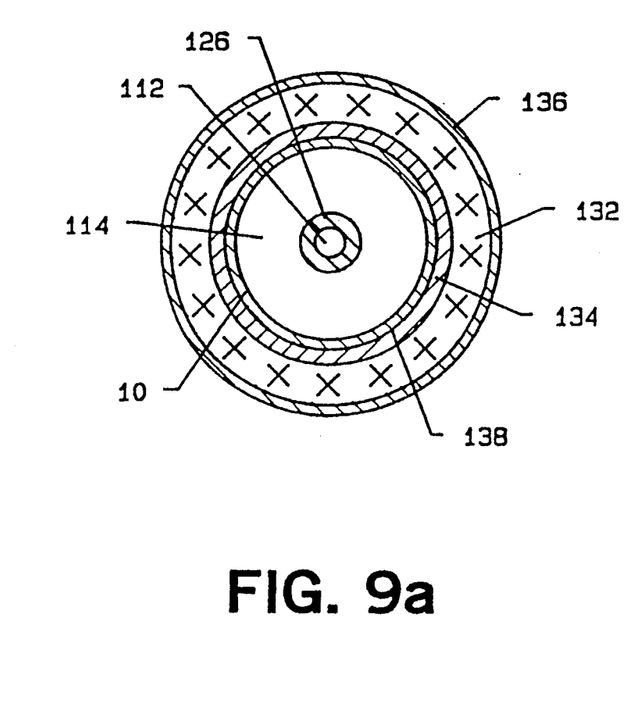
FIG. 9A illustrates a cross-sectional view taken along line 9a–9a of FIG. 8 of the coaxial configuration.

FIG. 9A illustrates a cross-sectional view taken along line 9a–9a of FIG. 8 where all numerals correspond to those elements previously described.

Figure 9B:
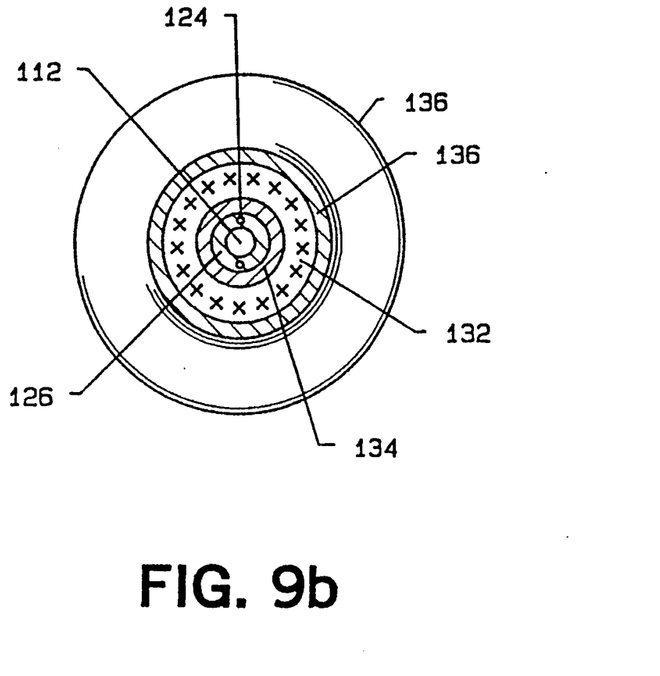
FIG. 9B illustrates a cross-sectional view taken along line 9b–9b of the coaxial configuration.

FIG. 9B illustrates a cross-sectional view taken along line 9b–9b of FIG. 8 where all numerals correspond to those elements previously described.

Figure 10:
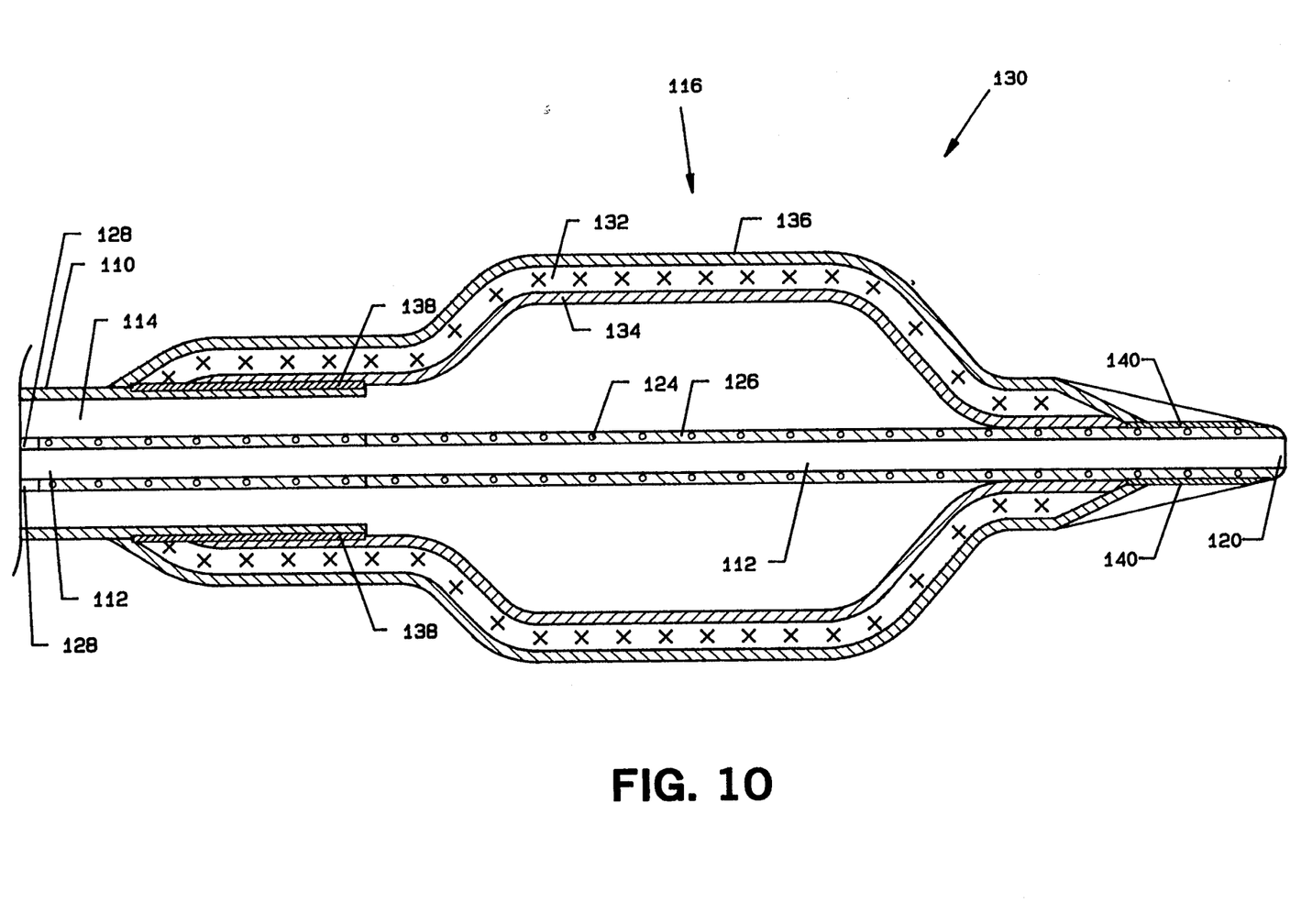
FIG. 10 illustrates the expanded balloon of the coaxial configuration.

FIG. 10 illustrates a balloon catheter 100, and particularly the balloon 130 in an inflated mode position. All numerals correspond to those elements previously described. The operation is similar to that as described for FIGS. 1–5.

DETAILED DESCRIPTION OF A SECOND ALTERNATIVE EMBODIMENT

Figure 11:
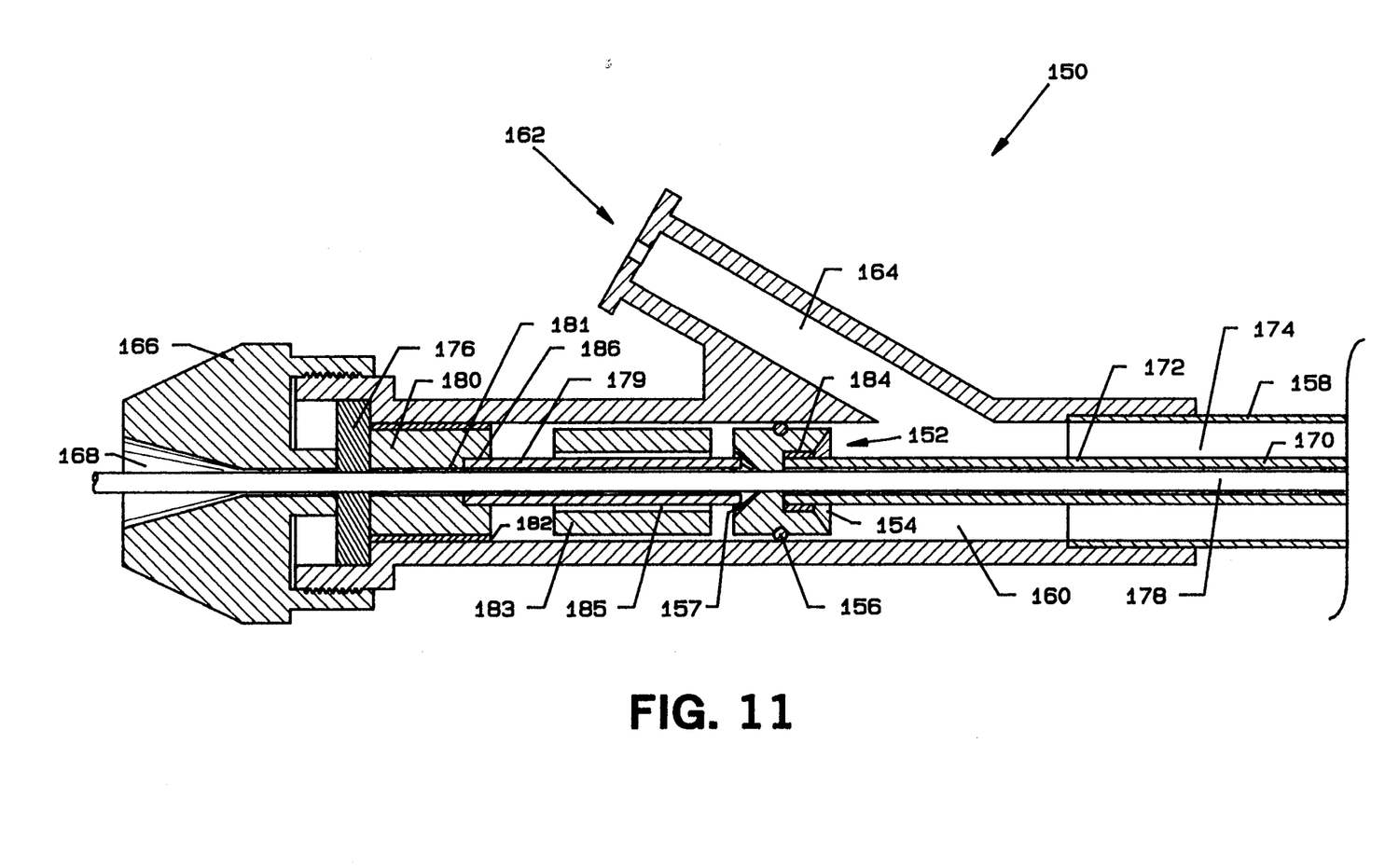
FIG. 11 illustrates a cross-sectional view of a hub including an additional sealing member of a first alternative embodiment.
Figure 12:
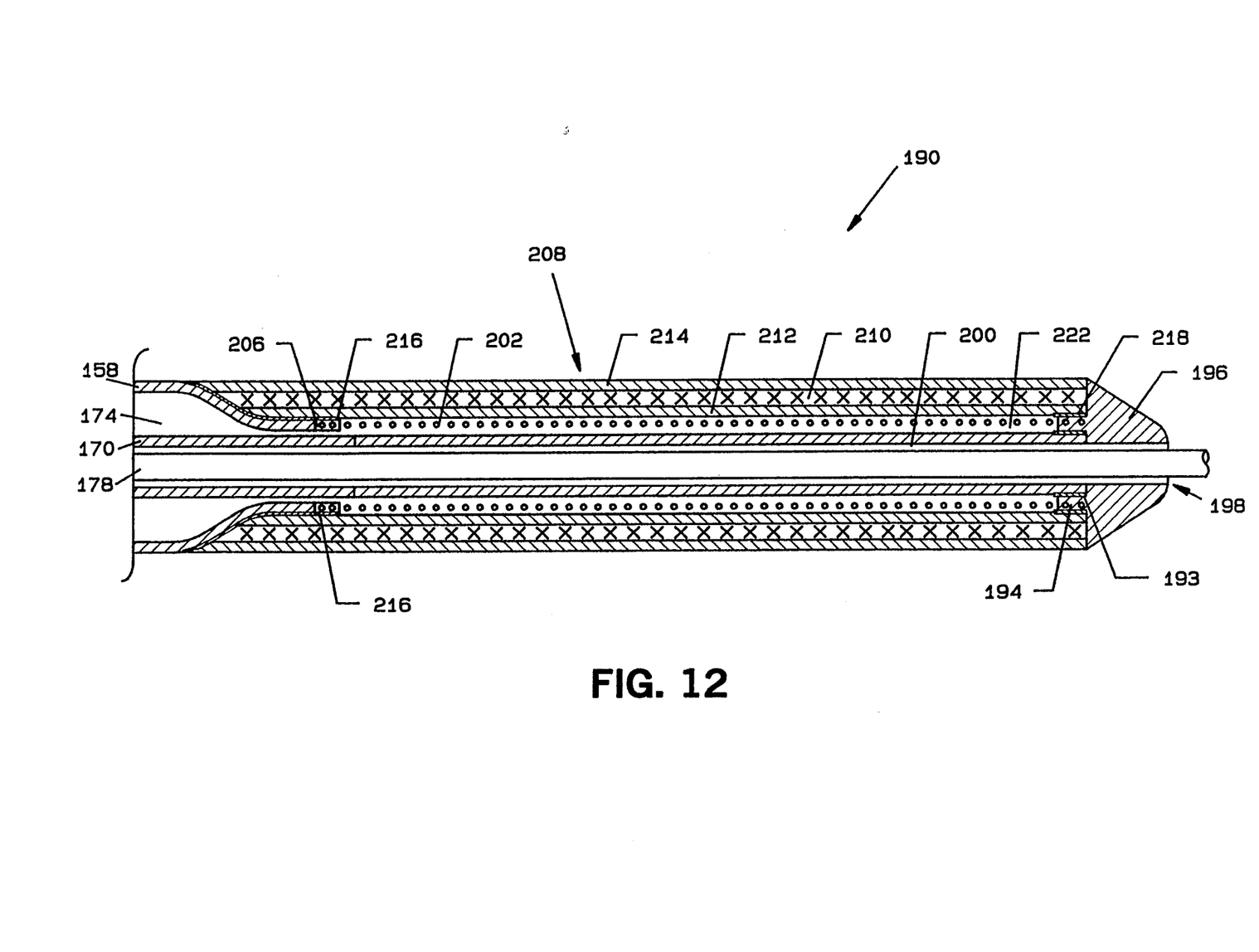
FIG. 12 illustrates a cross-sectional view of a distal end of a balloon catheter of a first alternative embodiment; and, FIG. 13 illustrates the balloon structure of FIG. 12 in the inflated position.

FIG. 11, a second alternative embodiment, illustrates a cross-sectional view of a hub 150 for use with a balloon catheter 190 such as illustrated in FIG. 12 which utilizes a sealing member 152 comprised of a piston 154, an 0-ring or quad ring 156, a tapered conical surface 151, and other members as now described. The figure illustrates the hub 150 being a molded member engaged about a tube 158 and fused or adhesively secured thereto. The hub 150 includes a hub chamber 160, an inflation/deflation port 162, an inflation/deflation chamber 164 between the inflation/deflation port 162 and the hub chamber 160, a cap 166 threadingly secured over the proximal end of the hub 150, and a guidewire entry port 168 centered through the axis of the cap 166. The proximal end of the tube 158 secures into one end of the hub 150. The hub 150, the tube 158, the guidewire entry port 168 and the inflation/deflation port 162 and associated members are assembled by known processes. An inner coaxially aligned elastomeric tube 170 aligns within the tube 158 and serves as a guidewire passage 172 and connects between a balloon structure such as balloon structure 116 of FIG. 8 or the balloon structure 208 of FIG. 12 and passes through the hub chamber 160 and secures to the piston 154 of the sealing member 152 as later described in detail. An inflation/deflation passage 174 is formed between the walls of the outer tube 158 and the tubular elastomeric material 170 in a coaxial fashion. The cap 166 is threaded onto the end of the hub 150 and compresses a seal 176 through which a guidewire 178 passes. A cylindrical stop cylinder 180, including a central bore 181, aligns at the proximal end of the hub chamber 160 and secures thereto by a bonding glue 182 or other suitable means. A stainless steel hypo tube 179 is form fit, press fit, bonded or otherwise secured to an annular recess 186 in the cylindrical stop cylinder 180 and extends to align with the tapered condical surface 156 of the sealing member 152. The hypo tube 179 provides for passage of the guidewire 178 through the various members, including a compressible rubber cylindrical buffer 188, a sealing member 152 and the elastomeric tube 170. A compressible rubber cylindrical buffer 183, such as silicone rubber, or soft plastic, and having a bore 185 slightly larger than the hypo tube 179 acts as a shock absorber and slidingly aligns over and about the stainless steel hypo tube 179. The piston 154 of the sealing member 152 slidingly engages the guidewire 178 and is secured to the proximal end of the elastomeric tube 170 by a bonding glue 184 or other suitable means. The overall length of piston 154, along with the length of the compressible rubber buffer 183, control the length of travel of the piston 154 and the elastomeric tubing 170. The 0-ring seal 156 about the piston 154 seals against the inner wall of the hub chamber 160 to provide a pressure seal between proximal and distal portions of the hub chamber 160. Pressurizing fluid injected into the inflation/deflation port 162 is sealed from the dry proximal end of the hub chamber 160 containing only air by the piston 154 and the O-ring seal 156 about the piston 154. As pressurization of the balloon takes place, the spring member of the balloon is compressed and the overall balloon length is shortened as the elastomeric tube 170 is slidingly projected in the proximal direction by piston action of the sealing member. The piston 154, the O-ring seal 156 and the elastomeric tube 170, accordingly slide proximally along the guidewire 178 in the hub chamber 160 until the point of maximum restricted balloon inflation or until the piston 154 causes the cylindrical rubber buffer 183 to compressingly engage the cylindrical stop cylinder 180. The sealing member 152 maintains inflational integrity of an attached balloon catheter allowing the balloon structure 208 pressure to remain proper and constant where prior art devices have not maintained proper and constant pressure due to leakage in areas such as the cap seal.

FIG. 12 illustrates a cross-sectional view of a distal end of a balloon catheter 190 having a spring in a free space tubular area which is unrestricted by embedding materials, such as for use with a hub 150, such as illustrated in FIG. 11. All other numerals correspond to those elements previously described. A tubular elastomeric member 170 is located along the longitudinal axis and aligns in and is bonded by a bonding glue 193 to the interior of a tubular member 194 extending from a soft and flexible molded tip 196. A guidewire passage 198 in the molded tip 196 aligns with the guidewire passage 200 central to the elastomeric tube 170 along the longitudinal axis. One end of a spring 202 is embedded in the tubular member 194 of the tip 196 and extends coaxially over and about and along the interior of the elastomeric tube 170 until it meets and connects to tube member 158. Tube member 158 flares downwardly to meet the proximal end of the spring 202 and is secured thereto by a plastic shrink tube connector 206 or by other suitable means. The spring 202 can also butt up against tube 158 without being bonded. A coaxial balloon structure 208 aligns coaxially over and about the elastomeric tube 170, the spring 202 and the flared end of the tube 158. The balloon structure 208 includes an inner braided fiber 210 between an inner elastomeric material 212 and an outer elastomeric material 214 secured about the necked down portion of the tube 158 and about the tubular extension member 194 of the tip 196, such as by heat fusion or adhesive bonding 216 and 218. Pressurized inflation fluid from the inflation/deflation passage 174 transmits pressure along the area 222 between the elastomeric tube 170 and the inner elastomeric material 212 in which the spring 202 resides to inflate the balloon structure 208 as illustrated in FIG. 13.

Figure 13:
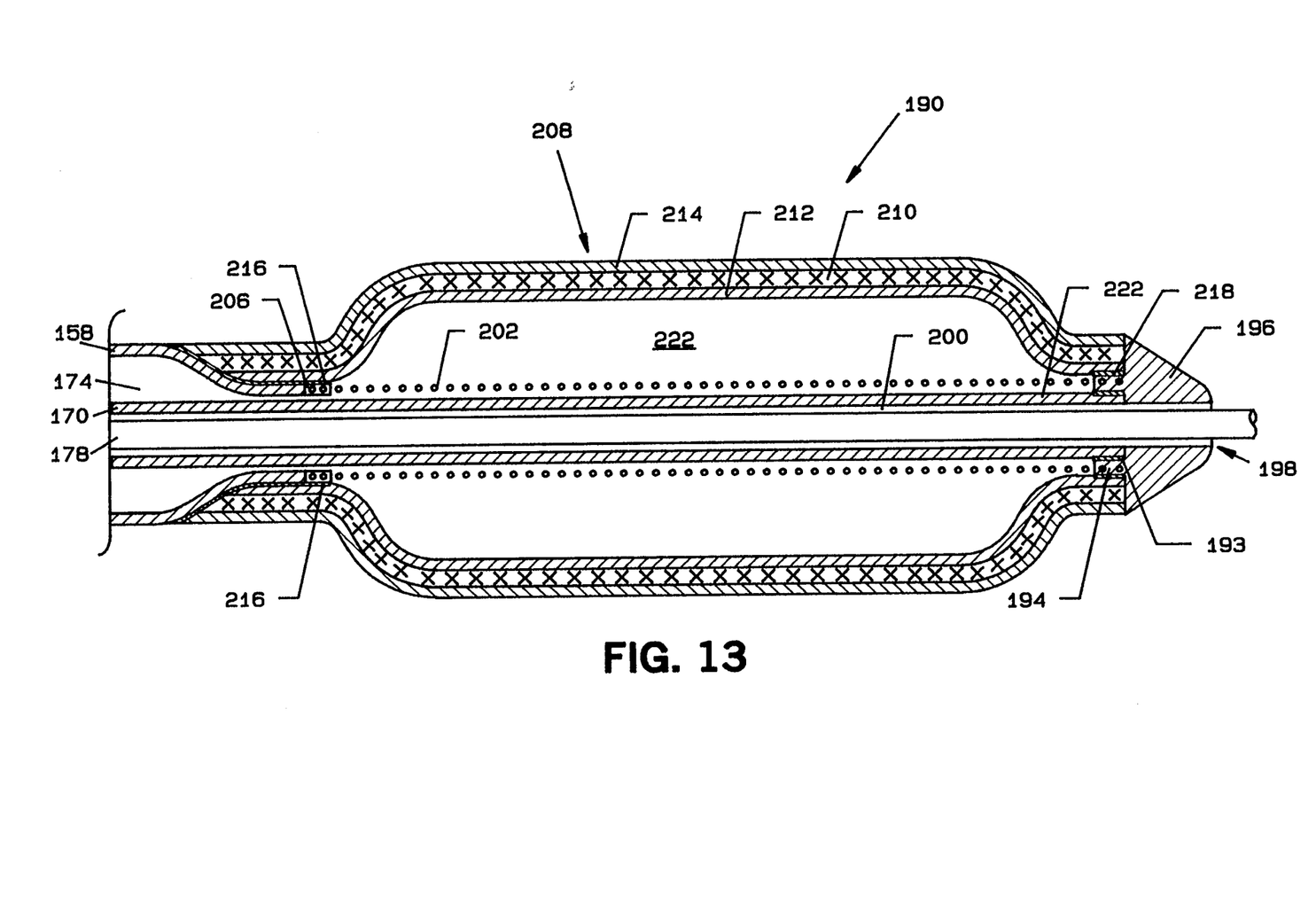

FIG. 13 illustrates the balloon structure in the inflated mode of operation where all numerals correspond to those elements previously described. The overall length of the distal end of the balloon catheter 190 is shortened during the inflation process due to the qualities of the elastomeric materials incorporated. The spring 202 is compressed along the longitudinal axis during inflation and expands along the longitudinal axis during deflation to aid and assist in returning the balloon structure 208 to the streamlined position as illustrated in FIG. 12.

MODE OF OPERATION OF THE SECOND ALTERNATIVE EMBODIMENT

The mode of operation of the second alternative embodiment is best described with reference to FIGS. 11, 12 and 13. First the maximum amount of expansion of the balloon catheter balloon structure 208 is determined. A hub 150 having a piston 154 and a rubber buffer cylinder 183 of suitable length is then chosen to accommodate the maximum amount of desired balloon structure 208 inflation. The hub 150 and the balloon catheter 190 are then fit over and slid over, about and along the guidewire 178 by known means until reaching the point of desired inflation. The cap 166 is then tightened on the hub threads to cause the seal 176 to compress about and to seal the guidewire 178, thus forming the primary seal of the hub chamber 160 at a point proximal to the sealing member 152. Saline solution is positive pressure fed through the inflation/deflation port 162 and travels through the inflation/deflation port 162 to the hub chamber 160. Positive pressure in the hub chamber is exerted in two directions, distally through the tube 158 to the balloon structure 208 and proximally toward the piston 154 of the sealing member 152. As positive system pressure increases, saline pressurizes the area 222 between the inner circumferential surfaces of the inner elastomeric material 212 causing the balloon structure 208 to expand outwardly to enlarge restricted blood vessels or arteries. Pressure exerted against the sealing member 152 drives the sealing member 152 a finite distance proximally until the sealing member 152 compresses the flexible rubber buffer 183 against the cylindrical stop cylinder 180. As the sealing member 152 is driven a finite distance proximally, the inner tube 170 also correspondingly moves proximally with respect to the tube 158 to position the balloon catheter tip 196 in a proximal direction. This action accomplishes several tasks. Firstly, the spring 202 is compressed, thus rendering the action of the spring 202 null and void for this part of the procedure. This is particularly important in that in the deflated mode, the spring tension which causes the balloon structure to become streamlined is overcome. Negating of the spring force cancels the stretching force along the length of the balloon structures 208 and allows the balloon structure 208 to be inflated outwardly without hindrance from an outstretched spring. Secondly, this action shortens the balloon structure 208, thus allowing a greater radius of expansion for the balloon structure 208 as it is suspended between two points 216 and 218 which are not fixed as in prior art devices, butt which are laterally moveable.

Deflation of the balloon is structure 208 accomplished in a reverse order. Pressure at the inflation/deflation port 162 is reduced to zero or can be reduced to a negative pressure if so required. The sealing structure 152 and the inner tube 170 then return to their relaxed mode position with the release of positive system pressure and with assistance from the compressed spring 202, which then returns to its normal length which also returns the balloon structure 208 to its original streamlined low profile position.

Various modifications can be made to the present invention without departing from the apparent scope hereof.

I claim:

1. A balloon catheter having physical characteristics and size suitable for use in a medical procedure comprising:
   a. a catheter tube having a guidewire passage and an inflation/deflation passage;
   b. a hub, affixed to the proximal end of said catheter tube, including a guidewire entry port connected to said guidewire passage and an inflation/deflation port connected to said inflation/deflation passage and including in order a stop cylinder and a shock absorber in a hub chamber of said hub;
   c. an elastomeric tube, having a nominal diameter approximating said catheter tube, affixed to a distal end of said catheter tube in communication with said guidewire passage to facilitate passage of a guidewire therethrough;
   d. an annular balloon fixedly formed at the distal end thereof and having a port in communication with said inflation/deflation passage of said catheter tube;
   e. a helical spring, coaxially positioned with respect to said elastomeric tube within the annulus of said balloon, affixed between said elastomeric tube and said catheter tube and adapted to be compressed by longitudinal shortening of said elastomeric tube induced by radial expansion of said balloon; and,
   f. said spring having a longitudinal force resisting compression for holding said elastomeric tube at a predetermined length to maintain said annular balloon in a smooth tubular shape about said elastomeric tube when said balloon is in the deflated condition.

2. The catheter of claim 1 wherein said helical spring is affixed to said elastomeric tube under partial compression and is adapted to be further compressed by longitudinal shortening of said elastomeric tube.

3. The catheter of claim 1 wherein expansion of said annular balloon causes compression of said helical spring.

4. The catheter of claim 1 wherein said longitudinal force maintains said balloon in a longitudinally stressed condition when deflated.

5. The catheter of claim 4 wherein said balloon is free from folds or wrinkles and provides a smooth external surface to the interior wall of a blood vessel when in the longitudinally stressed condition.

6. The catheter of claim 1 wherein said balloon includes reinforcement fibers secured to said distal end of said catheter tube and to the distal end of said elastomeric tube.

7. The catheter of claim 1 including a sealing member connected to a proximal end of said elastomeric tube.

8. A balloon catheter having physical characteristics and size suitable for use in a medical procedure comprising:
   a. a catheter tube having a guidewire passage and an inflation/deflation passage;
   b. a hub, affixed to the proximal end of said catheter tube, including a guidewire entry port connected to said guidewire passage and an inflation/deflation port connected to said inflation/deflation passage and including in order a stop cylinder and a shock absorber in a hub chamber of said hub;
   c. an elastomeric tube, having a nominal diameter approximating said catheter tube, a short length relative to said tube, affixed to a distal end of said catheter tube in communication with said guidewire passage to facilitate passage of a guidewire therethrough;
   d. an annular balloon formed and fixedly secured at a distal end and having a port in communication with said inflation/deflation passage of said catheter tube;
   e. a helical spring, coaxially positioned with respect to said elastomeric tube within the annulus of said balloon, affixed between said elastomeric tube and said catheter tube and adapted to be compressed by longitudinal shortening of said elastomeric tube induced by radial expansion of said balloon;
   f. said spring having a longitudinal force resisting compression for holding said elastomeric tube at a predetermined length to elastomeric tube at a predetermined length to maintain said annular balloon in a smooth tubular shape about said elastomeric tube when said balloon is in the deflated condition; and
   g. expansion of said annular balloon causes compression of said helical spring.

9. The catheter of claim 8 wherein said helical spring is affixed to said elastomeric tube under partial compression and is adapted to be further compressed by longitudinal shortening of said elastomeric tube.

10. The catheter of claim 8 wherein said longitudinal force maintains said balloon in a longitudinally stressed condition when deflated.

11. The catheter of claim 10 wherein said balloon is free from folds or wrinkles and provides a smooth external surface to the interior wall of a blood vessel when in the longitudinally stressed condition.

12. The catheter of claim 8 wherein said balloon includes reinforcement fibers secured to said distal end of said catheter tube and to the distal end of said elastomeric tube.

13. The catheter of claim 8 including a sealing member connected to a proximal end of said elastomeric tube.

14. A balloon catheter having physical characteristics and size suitable for use in a medical procedure comprising:
   a. a catheter tube having a guidewire passage and an inflation/deflation passage;
   b. a hub, affixed to the proximal end of said catheter tube, including a guidewire entry port connected to said guidewire passage and an inflation/deflation port connected to said inflation/deflation passage and including in order a stop cylinder and a shock absorber in a hub chamber of said hub;
   c. an elastomeric tube, having a nominal diameter approximating said catheter tube, a short length relative to said tube, affixed to a distal end of said catheter tube in communication with said guidewire passage to facilitate passage of a guidewire therethrough;
   d. an annular balloon fixedly formed at the distal end and having a port in communication with said inflation/deflation passage of said catheter tube;
   e. a helical spring, coaxially positioned with respect to said elastomeric tube within the annulus of said balloon, affixed between said elastomeric tube and said catheter tube and adapted to be compressed by longitudinal shortening of said elastomeric tube induced by radial expansion of said balloon; and,
   f. said spring having a longitudinal force resisting compression for holding said elastomeric tube at a predetermined length to elastomeric tube at a predetermined length to maintain said annular balloon in a smooth tubular shape about said elastomeric tube when said balloon is in the deflated condition; and
   g. said spring is affixed to said elastomeric tube under partial compression and is adapted to be further compressed by longitudinal shortening of said elastomeric tube.

15. The catheter of claim 14 wherein expansion of said annular balloon causes compression of said helical spring.

16. The catheter of claim 14 wherein said longitudinal force maintains said balloon in a longitudinally stressed condition when deflated.

17. The catheter of claim 16 wherein said balloon is free from folds or wrinkles and provides a smooth external surface to the interior wall of a blood vessel when in the longitudinally stressed condition.

18. The catheter of claim 14 wherein said balloon includes reinforcement fibers secured to said distal end of said catheter tube and to the distal end of said elastomeric tube.

19. The catheter of claim 14 including a sealing member connected to a proximal end of said elastomeric tube.

* * * * *